United States Patent
Anderson

(10) Patent No.: US 6,321,753 B1
(45) Date of Patent: Nov. 27, 2001

(54) TANNING RESTRAINT APPARATUS AND METHODS OF CONSTRUCTING AND UTILIZING SAME

(76) Inventor: Regina Anderson, 637 Hix Rd., Westland, MI (US) 48485

( * ) Notice: Subject to any disclaimer, the term of this patent is extended or adjusted under 35 U.S.C. 154(b) by 0 days.

(21) Appl. No.: 09/356,725

(22) Filed: Jul. 20, 1999

(51) Int. Cl.7 .................................................. A61B 19/00
(52) U.S. Cl. ......................... 128/869; 128/876; 128/882
(58) Field of Search .................................... 128/846, 869, 128/876, 882, 893, 894, DIG. 20

(56) References Cited

U.S. PATENT DOCUMENTS

| | | |
|---|---|---|
| 3,345,654 | 10/1967 | Noble . |
| 3,712,271 | 1/1973 | Greathouse . |
| 3,981,030 | 9/1976 | Turner . |
| 4,071,023 | 1/1978 | Gregory . |
| 4,090,268 | 5/1978 | Turner . |
| 4,133,604 | 1/1979 | Fuller . |
| 4,471,952 | 9/1984 | Spann . |
| 4,541,696 | 9/1985 | Winger . |
| 4,854,138 | 8/1989 | Charland . |
| 5,117,842 | 6/1992 | Bistrek et al. . |
| 5,418,991 | 5/1995 | Shiflett . |
| 5,655,264 | 8/1997 | Davancens et al. . |
| 5,664,291 | 9/1997 | Stoller . |

OTHER PUBLICATIONS

A page making reference to"Sunbather's Toe Ring", patented in 1973. (Possibly U.S. Patent 3,712,271, listed above.).

Primary Examiner—Michael A. Brown
(74) Attorney, Agent, or Firm—Carrier, Blackman & Associates; Joseph P. Carrier; William D. Blackman

(57) ABSTRACT

An apparatus for restraining the feet of a person while sunbathing to provide proper alignment of feet and legs during the tanning process, which apparatus may also serve as a retainer for eyeglasses when not being used to facilitate tanning. This apparatus includes a piece of material sewn into a long tubular member and a spring-loaded latch. The tubular member is fed through the spring-loaded latch to adjustably form one or more loops which are placed over the large toes of a person's feet wherein the large toes are held adjacent to one another. When not being used to facilitate tanning, the apparatus may be used to retain glasses on the head of a user. The ends of the tubular member grip the ends of the eyeglass temple portions when inserted therethrough.

11 Claims, 2 Drawing Sheets

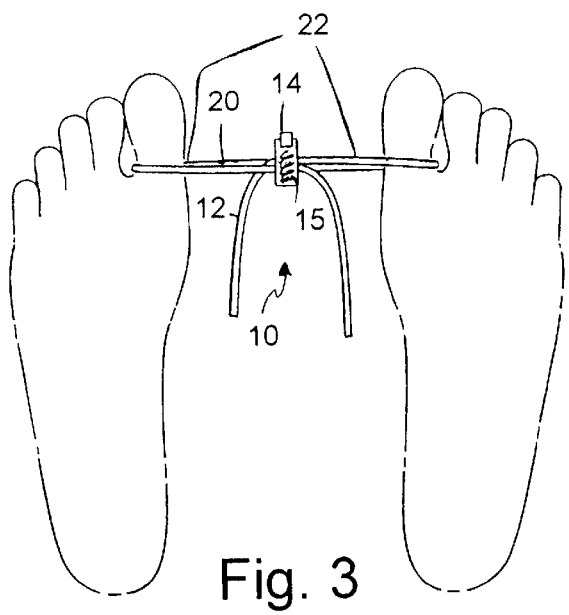
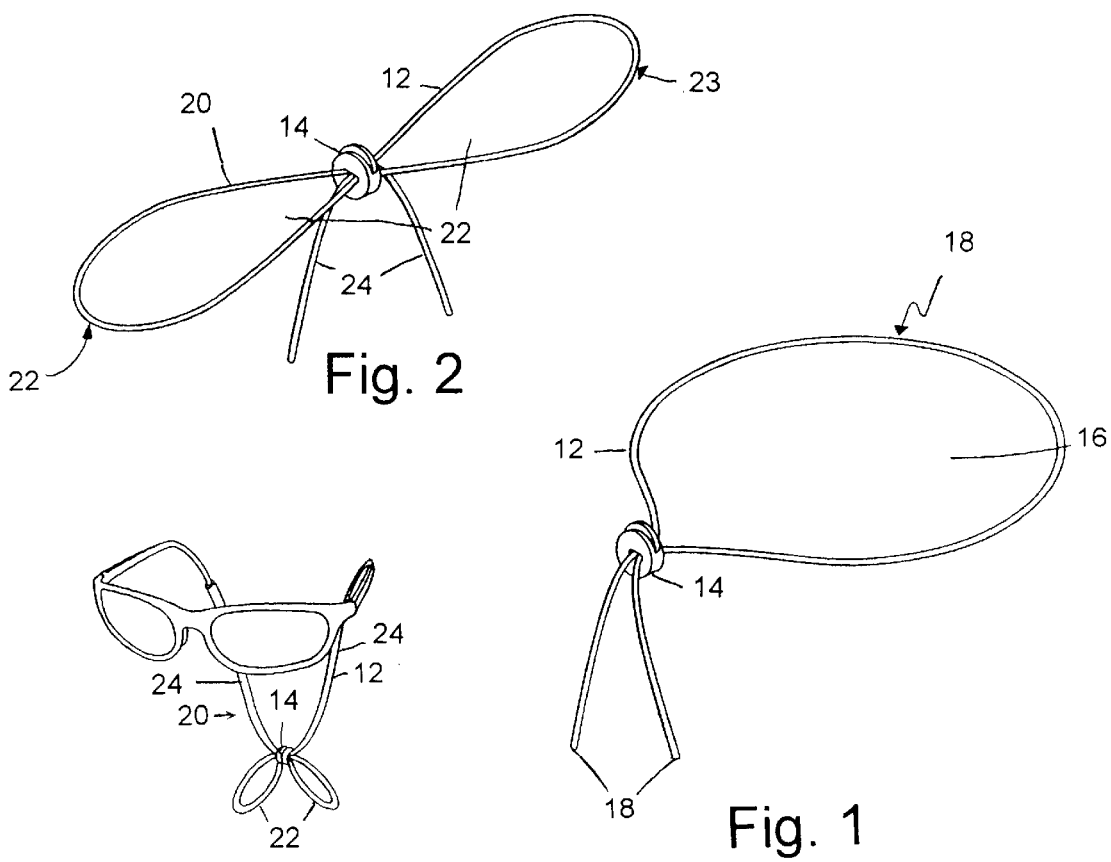

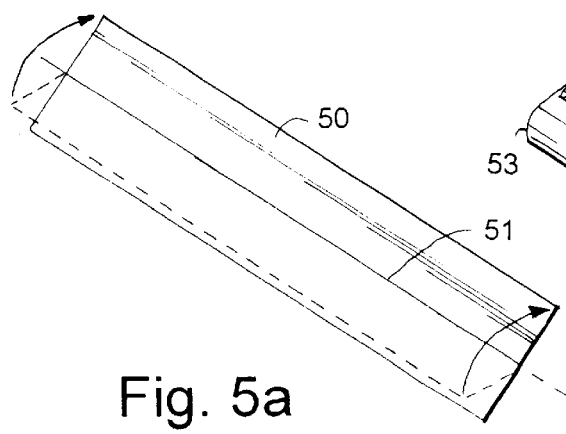
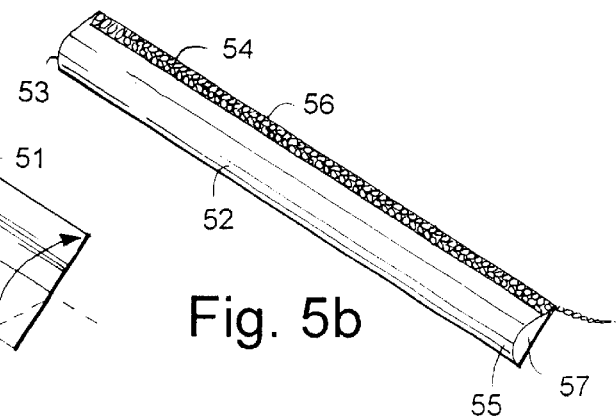
Fig. 5a
Fig. 5b
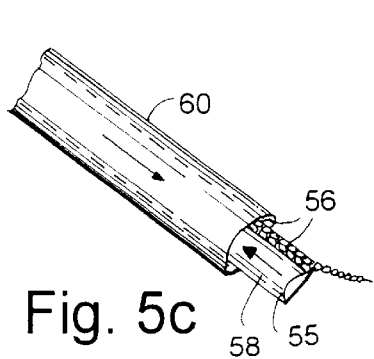
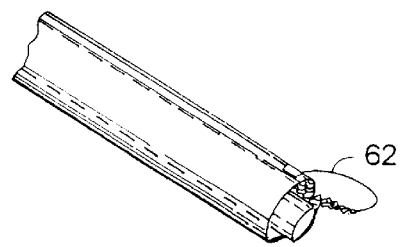
Fig. 5c
Fig. 5d
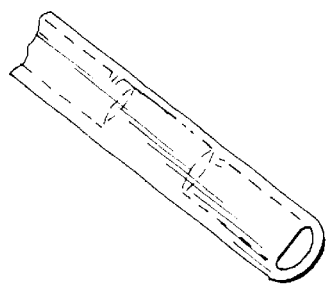
Fig. 5e

TANNING RESTRAINT APPARATUS AND METHODS OF CONSTRUCTING AND UTILIZING SAME

BACKGROUND OF THE INVENTION

1. Field of the Invention

The present invention relates to an apparatus for restraining the feet of a sunbathing person to provide proper orientation of feet and legs during the tanning process. More particularly, the present invention relates to such an apparatus which is simple, adjustable, and comfortable to use, and which apparatus may also serve as a retainer for eyeglasses when not being used to facilitate tanning.

2. Description of the Background Art

Some types of tanning restraint apparatus are known for aligning and restraining an individual's feet during the tanning process. Some of the known devices restrain a person's feet by means of a rigid apparatus; however, these apparatus do not provide adjustability for comfortable use by the wearer. Other devices are flexible and adjustable, but provide adjustability by means of comparatively complicated mechanisms.

Devices for restraining a person's feet or hands are also known for other non tanning uses, such as for law enforcement or medical purposes. These devices are made from rigid materials, and do not provide adjustability and comfortable use for the wearer.

None of the known apparatus serve the dual purpose of providing a foot alignment aid which also is useful for retaining eyeglasses when not employed in their primary function. Such a dual purpose provides the user a convenient means for carrying a tanning restraint apparatus and keeping it readily available, since many sunbathers use sunglasses and/or prescription glasses.

Known apparatus for retaining eyeglasses include tubular and non tubular members which attach to the eyeglass temple portions. Examples of some known tanning apparatus, other restraints, and eyeglass holders are discussed below:

U.S. Pat. No. 5,664,291 issued in 1997 to Stoller entitled "RETAINER AND HANGER FOR LENSES CONTAINING DEVICES", discloses a retainer for eyeglasses which includes short tubular members for engaging the eyeglass temple portions, an elastomeric cord connected to ends of the tubular members, and friction blocks slidingly provided on the cord between ends of the cord and the tubular members. The friction blocks can be positioned and retained on different parts of the cord according to a unique construction thereof.

U.S. Pat. No. 5,655,264 issued in 1997 to Davancens et al. entitled "END FASTENER FOR EYEGLASS HOLDERS", discloses an end fastener which may be provided on the ends of a cord or the like for engaging and retaining the temple portions of a pair of eyeglasses.

U.S. Pat. No. 5,117,842 issued in 1992 to Bistrek entitled "TANNING TETHER APPARATUS", discloses apparatus for use in tanning including an elongate tether formed into a main loop of flexible material with a pair of sliding cylinders provided over ends thereof to define a pair of adjustable size loops by the end portions of the main loop outward of the sliding cylinders. Also, an optional pair of heel pads may be attached to the sliding cylinders by tethers; while, the toe-engaging outer loops may be replaced with inflatable cylinders.

U.S. Pat. No. 4,854,138 issued in 1989 to Charland entitled "RESTRANG DEVICE", discloses a law enforcement device comprising a loop of fabric material which is secured to a locking block of plastic or the like such that a pair of adjustable size loops is defined by an intermediate portion of the fabric material. The locking block of material has openings and catches defined therein through which the cord may be moved only in one direction; and initially the loops are sized large enough to fit over a person's hands or legs, but once fitted thereover are reduced in size so as to securely restrain the person to whom they are attached.

U.S. Pat. No. 4,515,696 issued in 1985 to Winger et al. entitled "EYEGLASS RETAINER" and U.S. Pat. No. 4,133,604 issued in 1979 to Fuller entitled "EYEGLASS RETAINER", both disclose stretchable type retainers, such as CROAKIES (TM), formed of a material such as rubber or rubber foam and including tubular end portions, which securely retain the temple portions of eyeglasses when fitted thereover.

U.S. Pat. No. 4,071,023 issued in 1978 to Gregory entitled "RESTRAINING DEVICE", discloses another law enforcement restraining device. This device is made of plastic and may be adjusted to form two variable size loops which are fitted around an individual's wrists or ankles, but adjustment may only be made in one direction which makes the loops smaller.

U.S. Pat. No. 3,712,271 issued in 1973 to Greathouse entitled "TOE HOLDER", discloses a device molded of plastic which is not adjustable, and includes an opening for applying a decoration thereto.

Although the known devices are useful for their intended purposes, a need still exists in the art for a tanning restraint apparatus to hold a person's feet adjacent to one another while tanning which is simple, adjustable, and comfortable to use. A need also exists for an alternate use of the apparatus while not in use for tanning, such as retaining eyeglasses.

SUMMARY OF THE INVENTION

The present invention has been developed to overcome the foregoing limitations and disadvantages of conventional tanning restraint apparatus, and to generally fulfill a need in the art for a tanning restraint apparatus which is simple, adjustable, and comfortable to use. In a preferred embodiment of the invention, the apparatus also provides an alternate use while not in use for tanning, such as retaining eyeglasses.

According to the invention, there is provided a tanning restraint apparatus for restraining a person's feet adjacent to one another while tanning, including an elongate band, and a latch mechanism through which the ends of the band are secured so as to form a loop of the band. The latch mechanism is selectively adjustable between a locked position thereof, in which the ends of the band are firmly secured by the latch mechanism, and an unlocked position in which the ends of the band can be moved relative to the latch mechanism for varying a size of the loop. The ends of the band are preferably adapted to grippingly receive eyeglass temple portions therein.

It is preferable that the band is formed of a unitary piece of flexibly elastic sheet material sewn together at the edges to form a tubular shape, and folded over the longitudinal axis thereof, such that it includes a first tubular member and a second tubular member extending integrally from the first tubular member and disposed coaxially within the first tubular member. The preferable tubular shape allows the band to grippingly receive eyeglass temple portions therein, and the coaxial tubular members may further improve the eyeglass temple portion gripping ability of the band.

In different aspects of the invention, the ends of the band may be formed using a material different from that used in forming an intermediate portion of the band, or they may be formed of an elastomeric foam material. In other aspects of the invention, the ends of the band may include plastic tubes secured within the ends for gripping eyeglass temple portion portions, or the ends of the band may be thicker than the intermediate portion of the band.

In another aspect of the present invention, the ends of the band may be looped through the latch mechanism such that the band forms a pair of opposed loops, each of the loops being selectively adjustable in size when the latch mechanism is in the unlocked position thereof.

In yet another aspect of the present invention, the latch mechanism includes a biasing means for normally urging the latch mechanism to the locked position thereof.

It is preferable that a method of manufacturing an apparatus for orienting a sunbather's feet while tanning, in accordance with the invention, includes the steps of forming an elongate band, and securing the ends of the band through a latch mechanism so as to form at least one loop of the band. It is further preferable that the step of forming the band involves the following steps: folding a unitary piece of flexible material substantially in half along a longitudinal axis of the material; sewing along a lateral side of the folded material, whereby a tubular member is formed, the tubular member having a hollow passage defined therein and having a pair of ends; folding the tubular member over the outside of itself, such that the tubular member is made up of a first tubular member and a second tubular member extending integrally from the first tubular member and disposed coaxially within the first tubular member; attaching the ends of the tubular member to one another; and drawing the attached ends within the first tubular member. It is also preferable that serge stitches are used for the step of sewing along a lateral side of the folded material.

Accordingly, it is an object of the present invention to provide a method and apparatus for simply, adjustably, and comfortably restraining the feet of a tanning person.

It is a further object of the present invention to provide an alternate use for a tanning restraint apparatus as well as a method for retaining eyeglasses.

It is another object of the present invention to provide methods for manufacturing simple, adjustable, and comfortable tanning restraint apparatus.

For a more complete understanding of the present invention, the reader is referred to the following detailed description section, which should be read in conjunction with the accompanying drawings. Throughout the following detailed description and in the drawings, like numbers refer to like parts.

BRIEF DESCRIPTION OF THE DRAWINGS

FIG. 1 is a perspective view of a tanning restraint apparatus in accordance with the first preferred embodiment of the present invention.

FIG. 2 is a perspective view of a tanning restraint apparatus in accordance with the second preferred embodiment of the present invention.

FIG. 3 is an end plan view of a person's feet having a tanning restraint apparatus in accordance with the second preferred embodiment of the present invention attached thereto.

FIG. 4 is a perspective view of a pair of eyeglasses having a tanning restraint apparatus in accordance with the second preferred embodiment attached thereto.

FIGS. 5a–5e are perspective views of a tanning restraint apparatus at different stages of the preferred method for manufacturing the restraint apparatus, in accordance with the preferred embodiment of the method according to present invention.

DETAILED DESCRIPTION OF THE PREFERRED EMBODIMENTS

Referring to FIG. 1, there is shown a tanning restraint apparatus, according to the first preferred embodiment of this invention, for orienting a sunbather's feet while tanning. The apparatus 10 generally includes an elongate band 12, and a latch mechanism 14 through which the end portions of the band 12 are secured so as to form a loop 16 of the band 12. The latch mechanism 14 is selectively adjustable between a locked position thereof, in which the end portions 18 of the band 12 are firmly secured by the latch mechanism 14, and an unlocked position in which the end portions 18 of the band 12 can be moved relative to the latch mechanism 14, for varying a size of the loop 16.

The elongate band 12 is preferably formed of a unitary piece of flexibly elastic sheet material sewn into a tubular shape. The sheet material is preferably elastically deformable type bathing suit material or the like, such as "Spandex" material, but other elastic materials may also be suitable. Alternatively, the elongate band 12 may also be made from latex tubing or other rubberized compounds commonly available.

It is desirable that the band 12 be folded over its own longitudinal axis and sewn together to form a tubular shape, to facilitate an alternate use of the tanning restraint apparatus for retaining eyeglasses; however, a tubular shape is not necessary and eyeglass retention may be achieved using a different shaped hollow band. Also, the ends 18 alone could be sewn into a tubular shape to facilitate eyeglass retention and the intermediate portion may be flat similar to CROAKIES (TM) style eyeglass retainers. Alternatively, eyeglass retention may be achieved through the use of other eyeglass retention members attached to the elongate band 12.

In an alternative tubular shape construction, the elongate band 12 may be constructed to include a first tubular member and a second tubular member extending integrally from the first tubular member and disposed coaxially within the first tubular member. A tube within a tube, or coaxial tube construction, further improves the eyeglass temple portion gripping ability of the band without the use of additional eyeglass retention members or materials.

Improved eyeglass retention may be achieved by using a different material to form the ends of the elongate band 12 from that used in forming an intermediate portion of the band. This could be accomplished by sewing a more rigid material than the preferred "Spandex" type swimming suit material to the end regions of the flexible elastic sheet prior to sewing into a tubular form. Such rigid material could include thermoplastic materials in sheet form.

Additionally, the ends may be formed of an elastomeric foam material to improve eyeglass retention. Such a material in tubular form could be sewn onto the ends of the elongate band 12 after it is formed into a tube.

The ends of the elongate band 12 may also include plastic tubes secured onto end portions of the band material for improved gripping of the eyeglass temple portions. Such tubes may be sewn onto the ends of the elongate band 12, or may be placed coaxially over or coaxially within a portion of the ends of the elongate band 12, and secured using glue or other like means. Improved eyeglass retention may also be achieved by using thicker sheet material in the end regions of the elongate band 12 than in the intermediate portion. This could also be accomplished by sewing additional layers of sheet material to the end regions prior to sewing into a tubular member.

The latch mechanism 14 is preferably substantially constructed of plastic, because of its lightweight and non corrosive properties, but may be constructed substantially of steel, aluminum, or other rigid material. The latch mechanism preferably includes a spring or other biasing means for normally urging the latch mechanism 14 to a locked position for retaining the elongate band 12. Such preferable devices are common in industry as spring-loaded latches for securing cords of various configurations, but a wide variety of other type latches could however be used.

Preferable latches used in industry typically include a first and a second member, each having a transverse slot therein, and a biasing mechanism. The second member is typically slidingly located within the first member. In the unlatched configuration, each of their transverse slots aligns such that a cord or other elongate member may be placed through both slots. In the latched configuration, a biasing member longitudinally, slidingly biases the second member relative to the first member, such that the transverse slots become misaligned and thereby grip any elongate member placed therein. The latched configuration is the default position for these latches due to the action of the biasing member. To unlatch, one merely biases the second member slidingly in the direction contrary to the biasing member's action until the slots are aligned. Typically, this only requires a person to grip the latch between a finger and a thumb of one hand and squeeze, placing pressure on the second member in its longitudinal direction.

In the first preferred embodiment, shown in FIG. 1, the ends of the elongate band 12 are placed through the latch from the same direction, and secured by the latch mechanism 14 to form a single loop 16. For use in restraining one's feet to properly orient them for tanning, a sunbather simply places the loop 16 over each large toe of each foot. In order to adjust for comfort or to achieve the desired orientation of their feet, the sunbather merely squeezes the latch mechanism 14, as described above, which places it in an unlatched position and allows adjustment of the loop size. After adjustment to the desired size, the sunbather simply releases the latch mechanism, which will default to a latched configuration.

For use in retaining eyeglasses, a terminal end of each eyeglass temple portion is inserted longitudinally through an end 18 of the elongate band 12 formed into a tubular member. As discussed above, other members may be attached to the end's 18 of the elongate band 12 for retention of eyeglasses, but the preferred embodiment is for the elongate band 12 to be formed into a tubular member, with appropriate elastic properties, for retention of eyeglasses. To minimize the size of the loop 16 and thereby extend the length of the end portions of the elongate band 12, the user simply unlatches the latching mechanism as described above and simultaneously moves the elongate band 12 through the latch until the desired loop size and configuration is achieved.

Referring to FIGS. 2, 3, and 4, there is shown a tanning restraint apparatus for orienting a sunbather's feet while tanning according to the second preferred embodiment of this invention. In this second embodiment, the band 12 and the latch 14 are substantially the same as previously described, but are arranged in a different configuration such that the elongate band 12 forms a pair of opposed loops 22. Each of the loops 22 is selectively adjustable in size when the latch mechanism 14 is in the unlocked position thereof.

The second preferred embodiment is created by engaging the latch mechanism 14 such that it is in the unlocked position, and then threading an end of the elongate band 12 through the latch mechanism 14 until an intermediate point on the elongate band 14 is located through the latch mechanism 14. While continuing to maintain the latch mechanism 14 in the unlocked position, each end 18 of the elongate band 12 is then threaded through the latch mechanism 14 from opposing directions whereby two opposed loops 22, 23 are formed. Releasing the latch mechanism 14 preferably returns it to a locked position which then maintains the elongate band 12 in its two loop configuration, each loop 22 being independently, selectively adjustable in size by unlocking the latch mechanism 14.

Referring specifically to FIG. 3, when using the apparatus 10 for use in restraining one's feet to properly orient them for tanning, a sunbather simply places one loop 22 over each large toe of each foot. In order to adjust for comfort or to achieve the desired orientation of one's feet, the sunbather merely squeezes the latch mechanism 14, as described above, which places it in an unlatched position and allows adjustment of the loop sizes. After adjustment to the desired sizes, the sunbather merely releases the latch mechanism, which will default to a latched configuration.

Referring specifically to FIG. 4, for use in retaining eyeglasses, as discussed above, each eyeglass temple portion is inserted longitudinally through an end 18 of the elongate band 12 formed into a tubular member. To minimize the size of the loops 22 and thereby extend the length of the end portions 24 of the elongate band 12, the user simply unlatches the latching mechanism as described above and simultaneously moves the elongate band 12 through the latch until the desired loop sizes and configuration are achieved.

Referring to FIGS. 1, and 5a through 5f, there is shown a preferred method for manufacturing the tanning restraint apparatus hereof. The method of manufacturing such apparatus generally includes the steps of forming an elongate band 12, and securing the end portions of such band 18 through a latch mechanism 14 so as to form at least one loop 16 of the band. It is further preferable that the step of forming the band 12 generally involve the following steps: folding a unitary piece of flexible material 50 substantially in half along a longitudinal axis 51 of the material; sewing along a lateral side 54 of the folded material 50, whereby a tubular member 52 is formed, the tubular member having a hollow passage 55 therein and a pair of ends 53; folding the tubular member 52 over the outside of the tubular member 52 such that the tubular member 52 comprises a second tubular member 58 disposed coaxially within a first tubular member 60; attaching the ends 53, 55 to one another; and drawing the attached ends 53 within the first tubular member 58. It is preferable that the step of forming the band further involves using a serge stitch 56 for sewing along a lateral side of the folded material 50, for improved elasticity.

As shown in FIG. 5a, the first step merely involves laying out a unitary piece of flexible material 50, previously cut into a long strip, and folding such material along a longitudinal axis 51, substantially in half back onto itself. Preferably the decorative side of the material, or the side desired to be seen in the finished elongate band, should be on the inside of the fold.

The second step shown in FIG. 5b includes sewing along a lateral side 54 of the folded material, whereby a tubular member 52 is formed, the tubular member having a pair of ends 53, 55, and having a hollow passage 57 defined therein. It is preferable that such sewing involves using a serge stitch 54 for sewing along a lateral side 56 of the folded material 50, for improved elasticity; however, other stitches may also be appropriate.

FIG. 5c shows the first end 53 of the tubular member 52 having been inverted, being folded over the outside of the tubular member 52, such that the tubular member 52 is then made up of a second tubular member 58 disposed coaxially within a first tubular member 60. This step is accomplished by folding one end 53 of the tubular member 52 outward and inverting it back onto itself. Such an end 53 is then pulled over the remainder of the tubular member 52 until a second tubular member 58 is disposed coaxially within a first tubular member 60, and the ends 53, 55 of the tubular member 52 are substantially co-located. This step places the decorative side of the material outward and hides the sewing stitches 56 within the tubular member 52.

The next step is to attach the ends 53, 55 of the tubular member 52 to one another. As shown in FIG. 5d, this is preferably accomplished by sewing opposing ends of a thread 62 to each end 53, 55 of the tubular member 52, but may be accomplished in many different ways. For example, the ends 53, 55 could be directly glued, sewn, clipped, or otherwise attached to one another, or a connecting member could be attached to each elongate end. Attaching the ends to one another creates a continuous tubular loop which is looped within itself along its longitudinal axis. The end result is a layered elongate band 12 which has improved gripping abilities for retaining the ends of eyeglasses as well as improved strength.

The final step in forming the elongate band 12, as shown in FIG. 5e is to draw the joined ends 53 within the first tubular member 60. This is accomplished by rolling the loop of material along its longitudinal axis to hide the attached ends. Other methods of forming a tube of material are possible, but this method creates an important continuous loop. The continuous loop design allows the attachment region to be rolled within the first tubular member such that all seams and connections are hidden and the ends 18 of the elongate band 12 are rolled. The attached ends 53 should be rolled within the first tubular member 60 a sufficient distance such that an eyeglass temple portion will not reach the attachment region when inserted through the elongate band 12.

The last step in manufacturing tanning restraint apparatus, as shown in FIG. 1 is to secure the ends 18 of elongate band 12 through a latch mechanism 14 so as to form at least one loop 16 of the band. This is accomplished as described above by unlatching the latch mechanism 14 and feeding the ends 18 of the elongate band 12 through the latch mechanism 14 to a desired point, and then latching the latch mechanism 14.

Although the present invention has been described herein with respect to preferred embodiments thereof, the foregoing description is intended to be illustrative, and not restrictive. Those skilled in the art will realize that many modifications of the preferred embodiments could be made which would be operable. All such modifications which are within the scope of the claims are intended to be within the scope and spirit of the present invention.

What is claimed is:

1. Apparatus for orienting a sunbather's feet while tanning, the apparatus comprising:

an elongate band; and a latch mechanism through which the ends of said band are secured so as to form a loop of the band;

said latch mechanism being selectively adjustable between a locked position thereof, in which the ends of said band are firmly secured by the latch mechanism, and an unlocked position in which the ends of the band can be moved relative to the latch mechanism for varying a size of the loop;

the ends of said band are tabular and adapted to grippingly receive eyeglass temple portions therein; and said band is formed of a unitary piece of flexibly elastic sheet material sewn into a tubular shape.

2. Apparatus as recited in claim 1, wherein said tubular shaped band includes a first tubular member and a second tubular member extending integrally from the first tubular member and disposed coaxially within the first tubular member.

3. Apparatus as recited in claim 1, wherein the ends of the band are looped through said latch mechanism such that said band forms a pair of loops, each of said loops being selectively adjustable in size when the latch mechanism is in the unlocked position thereof.

4. Apparatus as recited in claim 1, wherein said latch mechanism includes a biasing means for normally urging the latch mechanism to said locked position thereof.

5. Apparatus as recited in claim 1, wherein said ends of said bind receive the eyeglass temple portions coaxially therein.

6. Apparatus for orienting a sunbather's feet while tanning, the apparatus comprising:

an elongate band; and a latch mechanism through which the ends of said band are secured so as to form a loop of the band;

said latch mechanism being selectively adjustable between a locked position thereof, in which the ends of said band are firmly secured by the latch mechanism, and an unlocked position in which the ends of the band can be moved relative to the latch mechanism for varying a size of the loop;

the ends of said band are tabular and adapted to grippingly receive eyeglass temple portions therein; and said ends of the band are formed using a material different from that used in forming an intermediate portion of the band.

7. Apparatus as recited in claim 6, wherein the ends of the band are formed of an elastomeric foam material.

8. Apparatus as recited in claim 6, wherein the ends of the band include plastic tubes secured to the ends for gripping the eyeglass temple portion portions.

9. Apparatus as recited in claim 6, wherein the ends of the band are thicker than the intermediate portion of the band.

10. A method of manufacturing apparatus for orienting a sunbather's feet while tanning, the method comprising the steps of:

forming an elongate band; and securing ends of said band through a latch mechanism so as to form at least one loop of the band;

said step of forming the band involving:

folding a unitary piece of flexible material substantially in half along a longitudinal axis of said material;

sewing along a lateral side of said folded material, whereby a tubular member is formed, said tubular member having a hollow passage defined therein and having a pair of ends;

folding one end of said tubular member over and around the outside of the rest of said tubular member, such that said tubular member becomes a first tubular member and a second tubular member extending integrally from tie first tubular member and disposed coaxially within the first tubular member;

attaching said ends to one another;

drawing said attached ends within first tubular member.

11. A method of manufacturing apparatus as recited in claim 10, wherein said step of forming the band further involves using a serge stitch for sewing along a lateral side of folded material.

* * * * *